US012611338B2

(12) United States Patent
Sullivan

(10) Patent No.: US 12,611,338 B2
(45) Date of Patent: Apr. 28, 2026

(54) MULTIPLE USE DIAPER ASSEMBLY

(71) Applicant: Michelle Sullivan, Scarborough, ME (US)

(72) Inventor: Michelle Sullivan, Scarborough, ME (US)

( * ) Notice: Subject to any disclaimer, the term of this patent is extended or adjusted under 35 U.S.C. 154(b) by 326 days.

(21) Appl. No.: 18/229,771

(22) Filed: Aug. 3, 2023

(65) Prior Publication Data

US 2025/0041130 A1     Feb. 6, 2025

(51) Int. Cl.
*A61F 13/505*     (2006.01)
*A61F 13/551*     (2006.01)
*A61F 13/84*     (2006.01)

(52) U.S. Cl.
CPC ........ *A61F 13/505* (2013.01); *A61F 13/5512* (2013.01); *A61F 13/5519* (2013.01); *A61F 2013/55125* (2013.01); *A61F 2013/8402* (2013.01)

(58) Field of Classification Search
CPC ................ A61F 13/505; A61F 13/5512; A61F 13/5519; A61F 2013/55125; A61F 2013/8402; A61F 13/493; A61F 13/84
See application file for complete search history.

(56) References Cited

U.S. PATENT DOCUMENTS

| | | | | |
|---|---|---|---|---|
| 4,597,760 | A * | 7/1986 | Buell ..................... | A41B 13/04 |
| | | | | 604/397 |
| 6,108,823 | A * | 8/2000 | Danes ................... | A41B 13/04 |
| | | | | 2/403 |
| D476,741 | S | 7/2003 | Childress | |
| 6,623,466 | B1 * | 9/2003 | Richardson ....... | A61F 13/15211 |
| | | | | 604/385.19 |
| 6,793,649 | B1 * | 9/2004 | Fujioka ................. | A61F 13/474 |
| | | | | 604/385.101 |
| 7,569,038 | B1 | 8/2009 | Salem, Jr. | |
| 8,292,863 | B2 | 10/2012 | Donoho | |
| 8,702,673 | B1 * | 4/2014 | Jones .................... | A61F 13/505 |
| | | | | 604/386 |
| 9,901,494 | B2 | 2/2018 | Kurtiak | |
| 11,337,869 | B2 * | 5/2022 | Brownlee ........... | A61F 13/4704 |
| 2002/0165515 | A1 | 11/2002 | Burnham | |
| 2008/0119812 | A1 * | 5/2008 | Hurwitz ................ | A61F 13/493 |
| | | | | 604/385.01 |
| 2016/0008189 | A1 | 1/2016 | Ezzo | |
| 2019/0262197 | A1 | 8/2019 | Stewart | |

FOREIGN PATENT DOCUMENTS

WO      WO2007062161      5/2007

* cited by examiner

*Primary Examiner* — Susan S Su

(57)     ABSTRACT

A multiple use diaper assembly includes a first diaper and a first absorbent pad is attached to the first diaper to absorb bodily fluids from the user. A second diaper is removably attached to the first diaper which rests against the user when the first diaper and the second diaper are worn on the user. A second absorbent pad is attached to the second diaper to absorb bodily fluids from the user. A first pouch is attached to the first diaper and a second pouch is attached to the first diaper. A plurality of wipes is stored in the first pouch and each of the plurality of wipes is pre-moistened to clean the user of bodily fluids. A storage bag is contained in the second pouch thereby facilitating the second diaper to be disposed of.

7 Claims, 7 Drawing Sheets

25

58

54

11

56

60

MULTIPLE USE DIAPER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to diaper devices and more particularly pertains to a new diaper device which has a first diaper and a second diaper being removably attached to the first diaper. The second diaper is removable from the first diaper when the second diaper becomes soiled to facilitate the first diaper to be replaced on a user. The device includes a first pouch attached to the first diaper which contains a plurality of wipes and a second pouch attached to the first diaper which contains a storage bag for disposing of the second diaper.

(2) Description of Related Art Including Information Disclosed Under 37 CFR 1.97 and 1.98

The prior art relates to diaper devices including a variety of diapers which each includes a pouch attached to the diaper which stores a plurality of wipes. In no instance does the prior art disclose a diaper device that includes a first diaper and a second diaper that is removably attached to the first diaper as well as a first pouch containing wipes and a second pouch containing a storage bag for disposing of the second diaper.

BRIEF SUMMARY OF THE INVENTION

An embodiment of the disclosure meets the needs presented above by generally comprising a first diaper and a first absorbent pad is attached to the first diaper to absorb bodily fluids from the user. A second diaper is removably attached to the first diaper which rests against the user when the first diaper and the second diaper are worn on the user. A second absorbent pad is attached to the second diaper to absorb bodily fluids from the user. A first pouch is attached to the first diaper and a second pouch is attached to the first diaper. A plurality of wipes is stored in the first pouch and each of the plurality of wipes is pre-moistened to clean the user of bodily fluids. A storage bag is contained in the second pouch thereby facilitating the second diaper to be disposed of.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
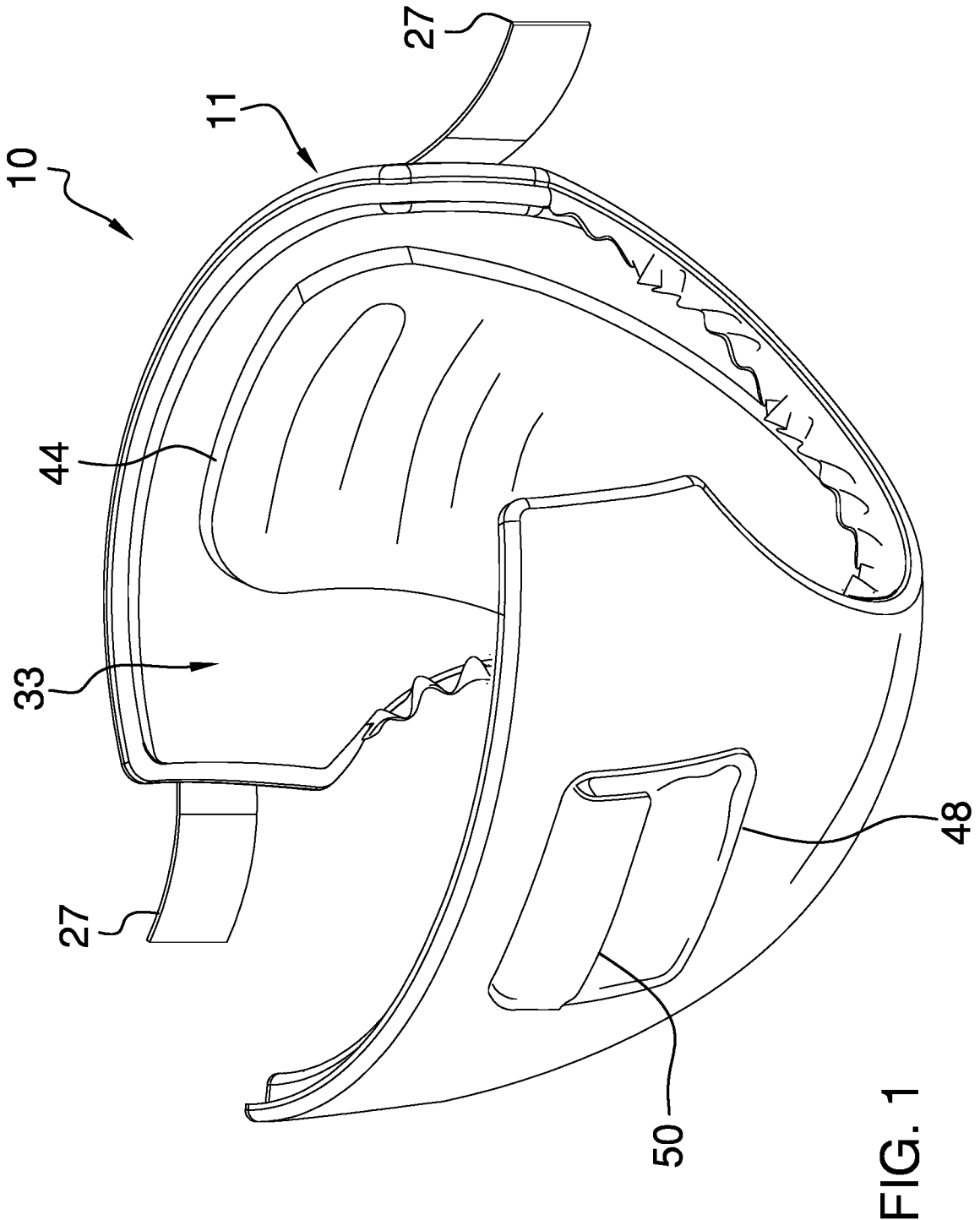
FIG. 1 is a front perspective view of a multiple use diaper assembly according to an embodiment of the disclosure.
Figure 2:
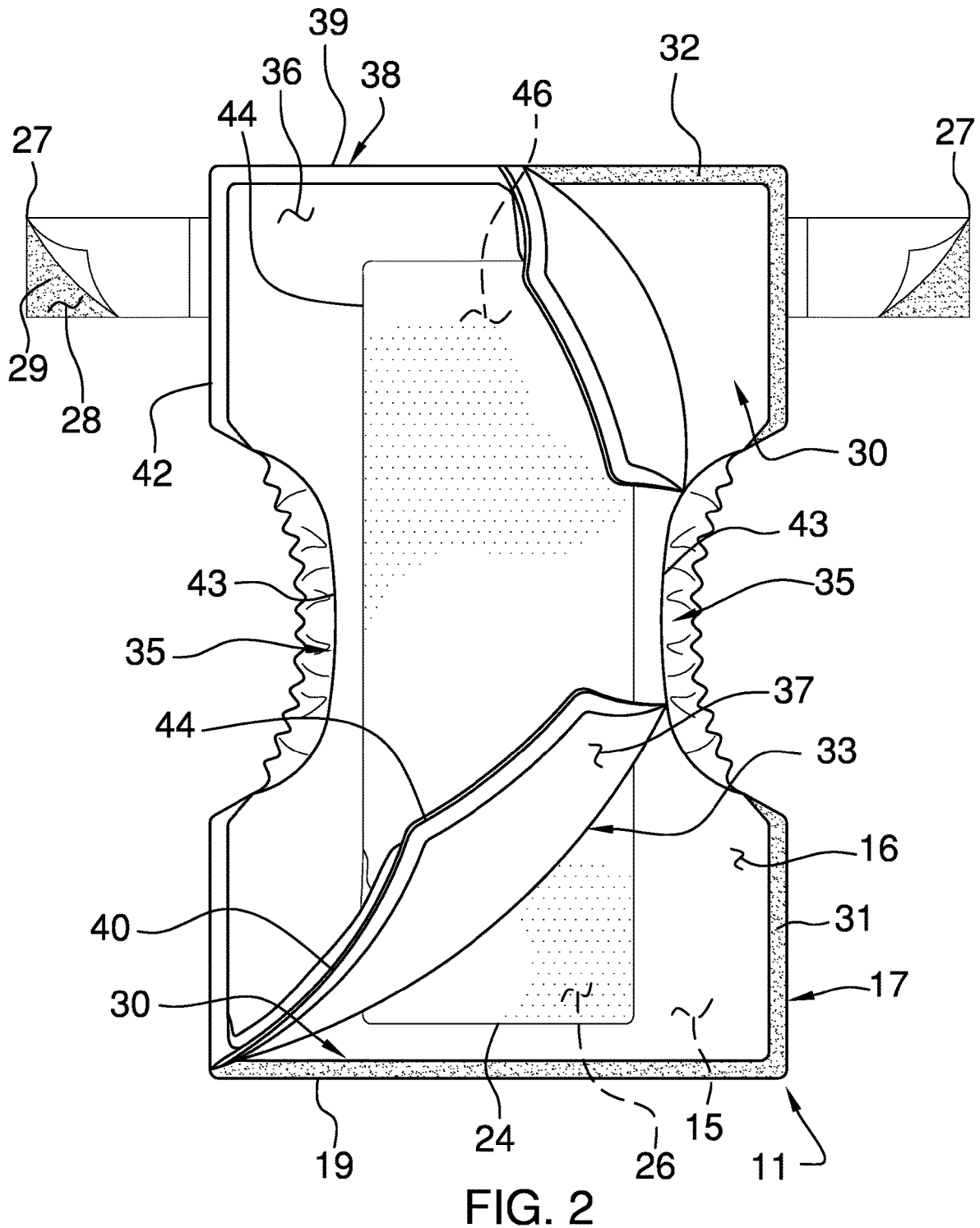
FIG. 2 is a top view of an embodiment of the disclosure.
Figure 3:
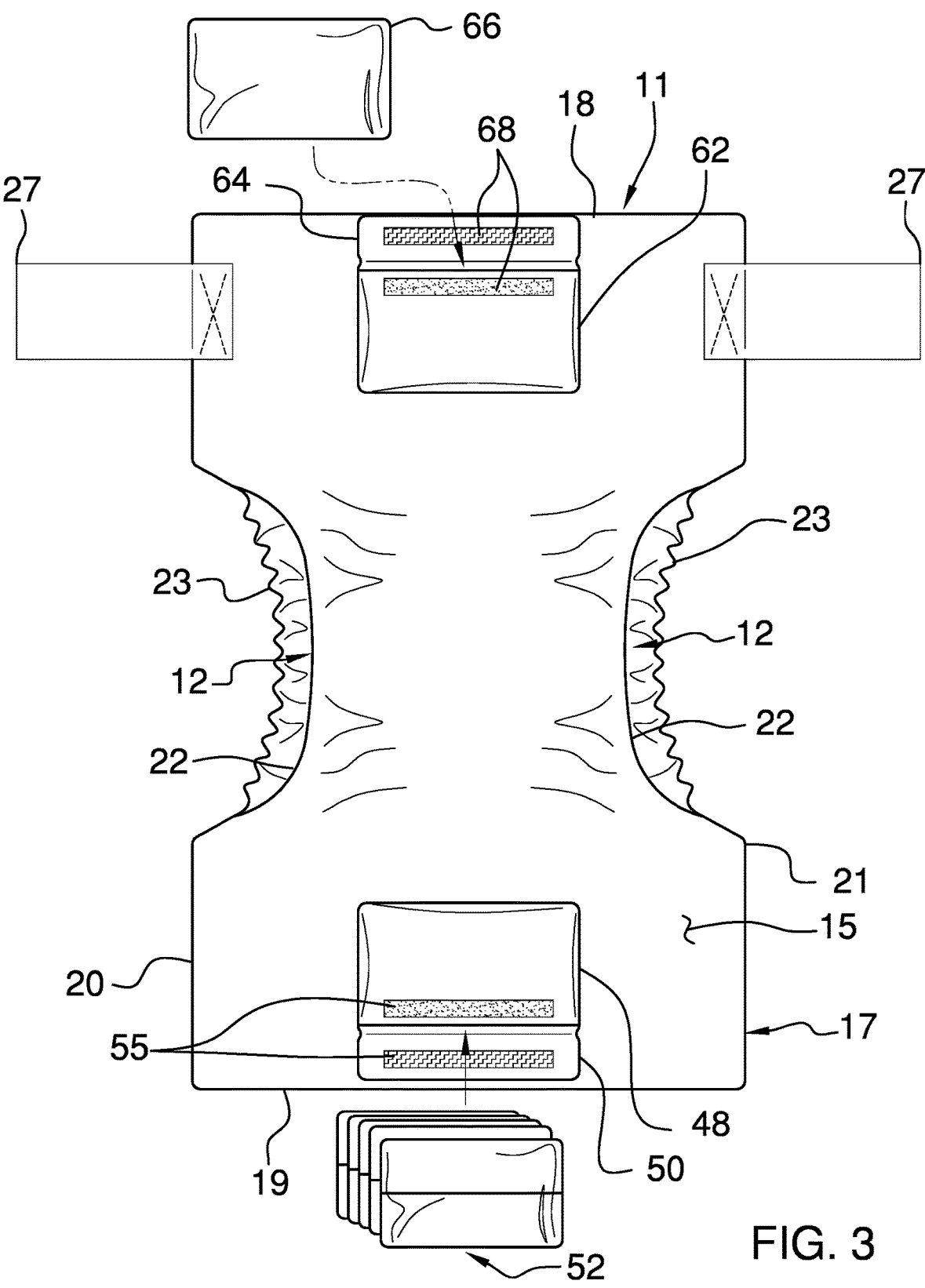
FIG. 3 is a bottom view of an embodiment of the disclosure.
Figure 4:
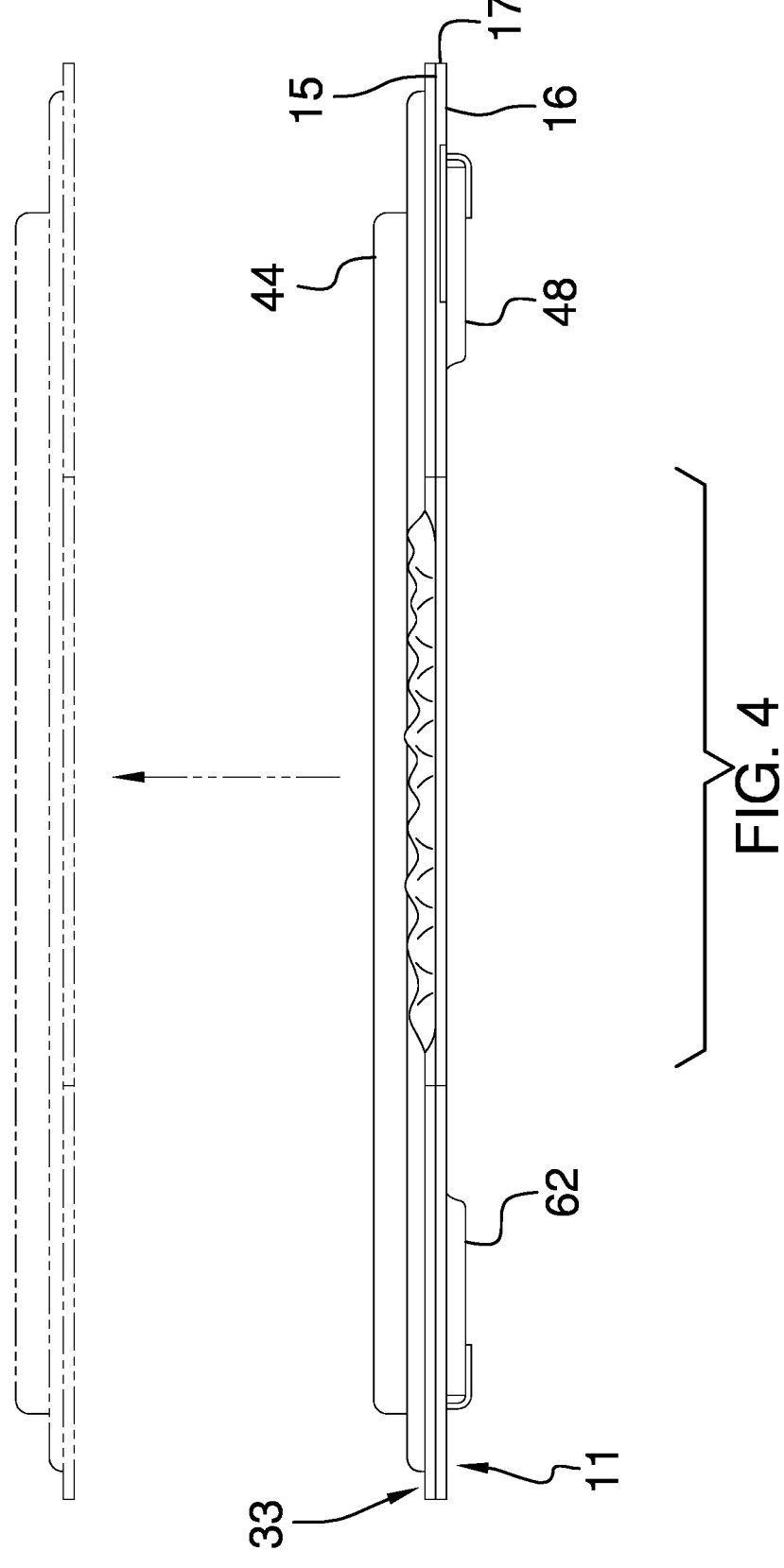
FIG. 4 is a right side view of an embodiment of the disclosure.
Figure 5:
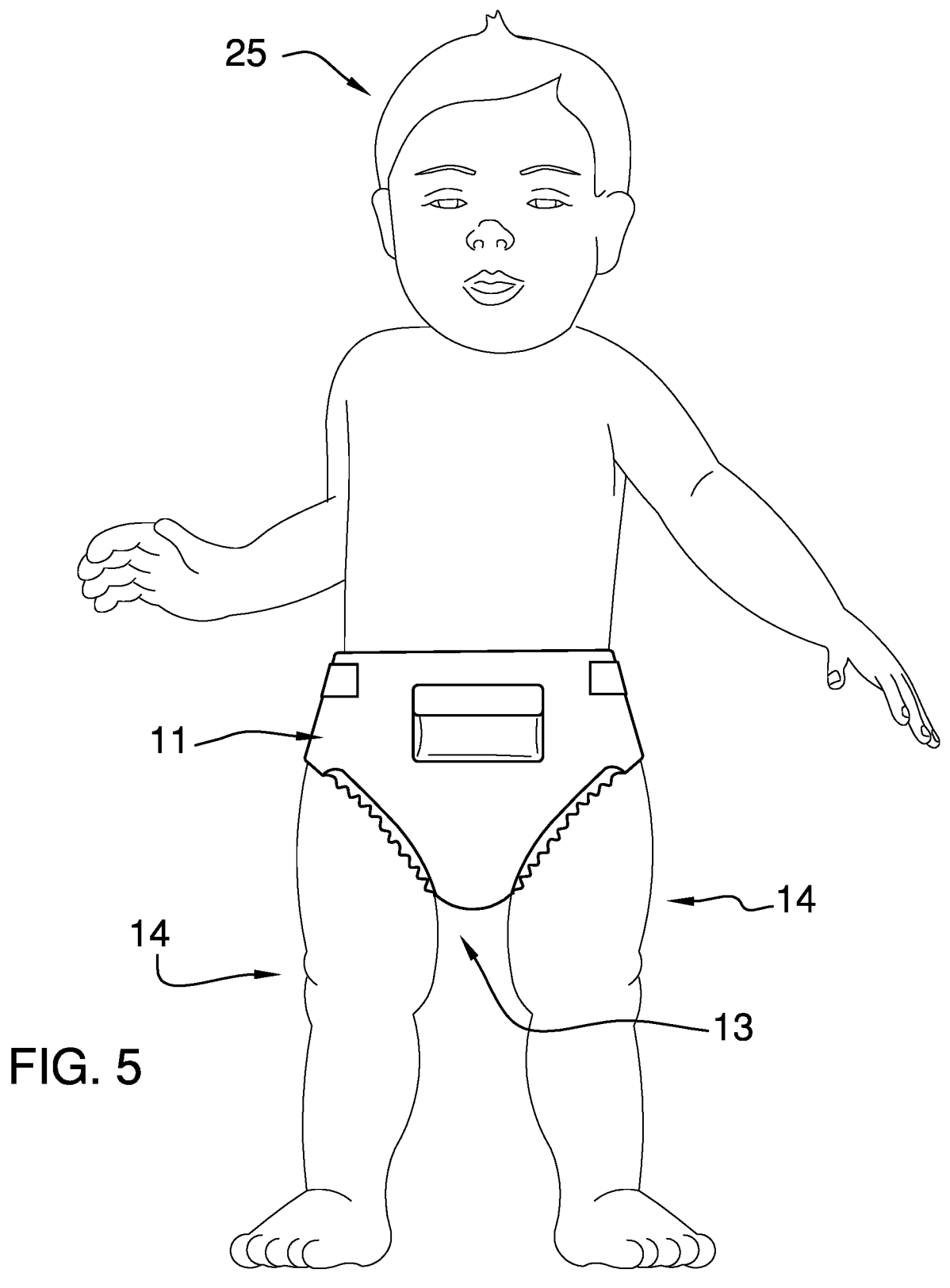
FIG. 5 is a front in-use view of an embodiment of the disclosure showing a first diaper and a second diaper being worn on an infant.
Figure 6:
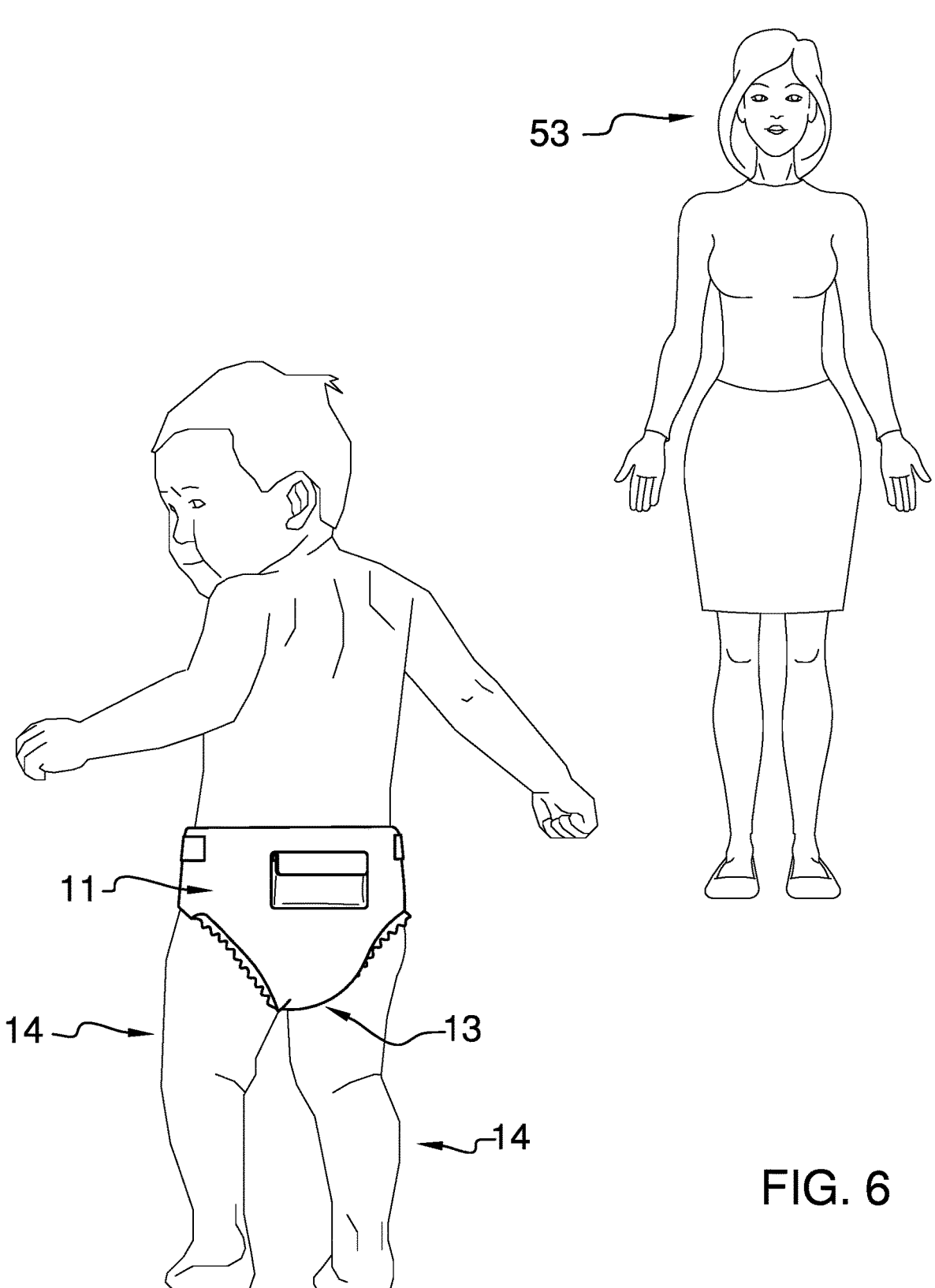
FIG. 6 is a perspective in-use view of an embodiment of the disclosure showing a first diaper and a second diaper being worn on an infant.

With reference now to the drawings, and in particular to FIGS. 1 through 7 thereof, a new diaper device embodying the principles and concepts of an embodiment of the disclosure and generally designated by the reference numeral 10 will be described.

As best illustrated in FIGS. 1 through 7, the multiple use diaper assembly 10 generally comprises a first diaper 11 that has a pair of leg scallops 12 thereby facilitating the first diaper 11 to be worn on a user's crotch 13 such that each of the leg scallops 12 accommodates a respective one of the user's legs 14. The first diaper 11 has a top surface 15 and a bottom surface 16 and a perimeter edge 17 extending between the top surface 15 and the bottom surface 16. The perimeter edge 17 has a top side 18, a bottom side 19, a first lateral side 20 and a second lateral side 21. Each of the first lateral side 20 and the second lateral side 21 has a curved portion 22 which curves toward each other such that curved portion 22 of each of the first lateral side 20 and the second lateral side 21 defines a respective one of the leg scallops 12. The curved portion 22 of each of the first lateral side 20 and the second lateral side 21 is centrally positioned between the top side 18 and the bottom side 19. The first diaper 11 is comprised of a fluid impermeable material, including but not being limited to polypropylene, to inhibit bodily fluids from passing through the first diaper 11.

A pair of elastomeric bands 23 is each attached to the top surface 15 of the first diaper 11. Each of the pair of elastomeric bands 23 is aligned with the curved portion 22 of a respective one of the first lateral side 20 and the second lateral side 21. In this way each of the pair of elastomeric bands 23 encloses each of the leg scallops 12 around the respective user's leg 14. A first absorbent pad 24 is attached to the first diaper 11 and the first absorbent pad 24 is comprised of a fluid absorbent material, including but not being limited to, cellulose. The first absorbent pad 24 is strategically located on the first diaper 11 thereby facilitating the first absorbent pad 24 to absorb bodily fluids from the user 25. The first absorbent pad 24 has a bonded surface 26 that is bonded to the top surface 15 of the first diaper 11 and the first absorbent pad 24 is elongated to extend substantially between the top side 18 and the bottom side 19 of the perimeter edge 17 of the first diaper 11. Additionally, the first absorbent pad 24 is centrally positioned between the first lateral side 20 and the second lateral side 21 of the perimeter edge 17.

A pair of tabs 27 is provided and each of the tabs 27 is attached to the first diaper 11. Each of the tabs 27 is wrappable onto the first diaper 11 when the first diaper 11 is being worn to retain the first diaper 11 on the user 25. Each of the tabs 27 is positioned on a respective one of the first lateral side 20 and the second lateral side 21 of the perimeter edge 17 of the first diaper 11 and each of the tabs 27 is positioned between the curved portion 22 of the respective first lateral side 20 and second lateral side 21 and the top side 18 of the perimeter edge 17. Furthermore, each of the tabs 27 has a first surface 28 and each of the pair of tabs 27 has an adhesive pad 29 that is applied to the first surface 28. The adhesive pad 29 on each of the pair of tabs 27 adhesively engages the bottom surface 16 of the first diaper 11 when the pair of tabs 27 are wrapped onto the first diaper 11.

A pair of adhesive strips 30 is each applied to the top surface 15 of the first diaper 11 and each of the pair of adhesive strips 30 is aligned with the perimeter edge 17 of the first diaper 11. A first one of the pair of adhesive strips 31 extends along the bottom side 19 of the perimeter edge 17 and along each of the first lateral side 20 and the second lateral side 21 of the perimeter edge 17 and terminates at the pair of elastomeric bands 23. A second one of the pair of adhesive strips 32 extends along the top side 18 of the perimeter edge 17 and along each of the first lateral side 20 and the second lateral side 21 of the perimeter edge 17 and terminates at the pair of elastomeric bands 23.

A second diaper 33 is removably attached to the first diaper 11 such that the second diaper 33 rests against the user 25 when the first diaper 11 and the second diaper 33 are worn on the user 25. The second diaper 33 has a pair of leg scallops 35 such that the pair of legs scallops 35 associated with the second diaper 33 accommodates the user's legs 14 when the first diaper 11 is worn on the user 25. The second diaper 33 is comprised of a fluid impermeable material, including but not being limited to polypropylene, to inhibit bodily fluids from passing through the second diaper 33. The second diaper 33 has an upper surface 36, a lower surface 37 and an outside edge 38 extending between the upper surface 36 and the lower surface 37. The outside edge 38 has an upper side 39, a lower side 40, a first sidelong side 41 and a second sidelong side 42.

Each of the first sidelong side 41 and the second sidelong side 42 has a curved portion 43 which curves toward each other such that curved portion 43 of each of the first sidelong side 41 and the second sidelong side 42 defines a respective one of the leg scallops 35 associated with the second diaper 33. Additionally, the curved portion 22 of each of the first sidelong side 41 and the second sidelong side 42 is centrally positioned between the upper side 39 and the lower side 40. The lower surface 37 of the second diaper 33 is adhered to each of the pair of adhesive strips 30 on the first diaper 11 thereby removably retains the second diaper 33 on the first diaper 11 having the outside edge 38 of the second diaper 33 is aligned with the perimeter edge 17 of the first diaper 11.

A second absorbent pad 44 is attached to the second diaper 33 and the second absorbent pad 44 is comprised of a fluid absorbent material, including but not being limited to cellulose, for absorbing bodily fluids. The second absorbent pad 44 is strategically located on the second diaper 33 to facilitate the second absorbent pad 44 to absorb bodily fluids from the user 25. The second absorbent pad 44 has a bonded surface 46 that is bonded to the upper surface 36 of the second diaper 33 and the second absorbent pad 44 is elongated to extend substantially between the upper side 39 and the lower side 40 of the outside edge 38 of the second diaper 33. Furthermore, the second absorbent pad 44 is centrally positioned between the first sidelong side 41 and the second sidelong side 42 of the outside edge 38. Each of the first diaper 11 and the second diaper 33 may be manufactured in a variety of sizes, ranging from infant to adult, thereby facilitating the first diaper 11 and the second diaper 33 to be employed for infants as well as incontinent adults.

A first pouch 48 is attached to the first diaper 11 and the first pouch 48 is applied to the bottom surface 16 of the first diaper 11. The first pouch 48 is spaced from the bottom side 19 of the perimeter edge 17 of the first diaper 11 and the first pouch 48 has a flap 50 that is foldable over the first pouch 48 for closing the first pouch 48. A plurality of wipes 52 is included and each of the plurality of wipes 52 is stored in the first pouch 48. In this way each of the plurality of wipes 52 is accessible to a caregiver 53 of the user 25 when the caregiver 53 removes the second diaper 33 from the first diaper 11 when the first absorbent pad 24 has become soiled with bodily fluids. Each of the plurality of wipes 52 is pre-moistened wherein each of the plurality of wipes 52 is configured to clean the user 25 of bodily fluids. A pair of first mating members 55 is each attached to a respective one of the flap 50 and the first pouch 48 and the pair of first mating members 55 is matable to each other for closing the first pouch 48.

Figure 7:
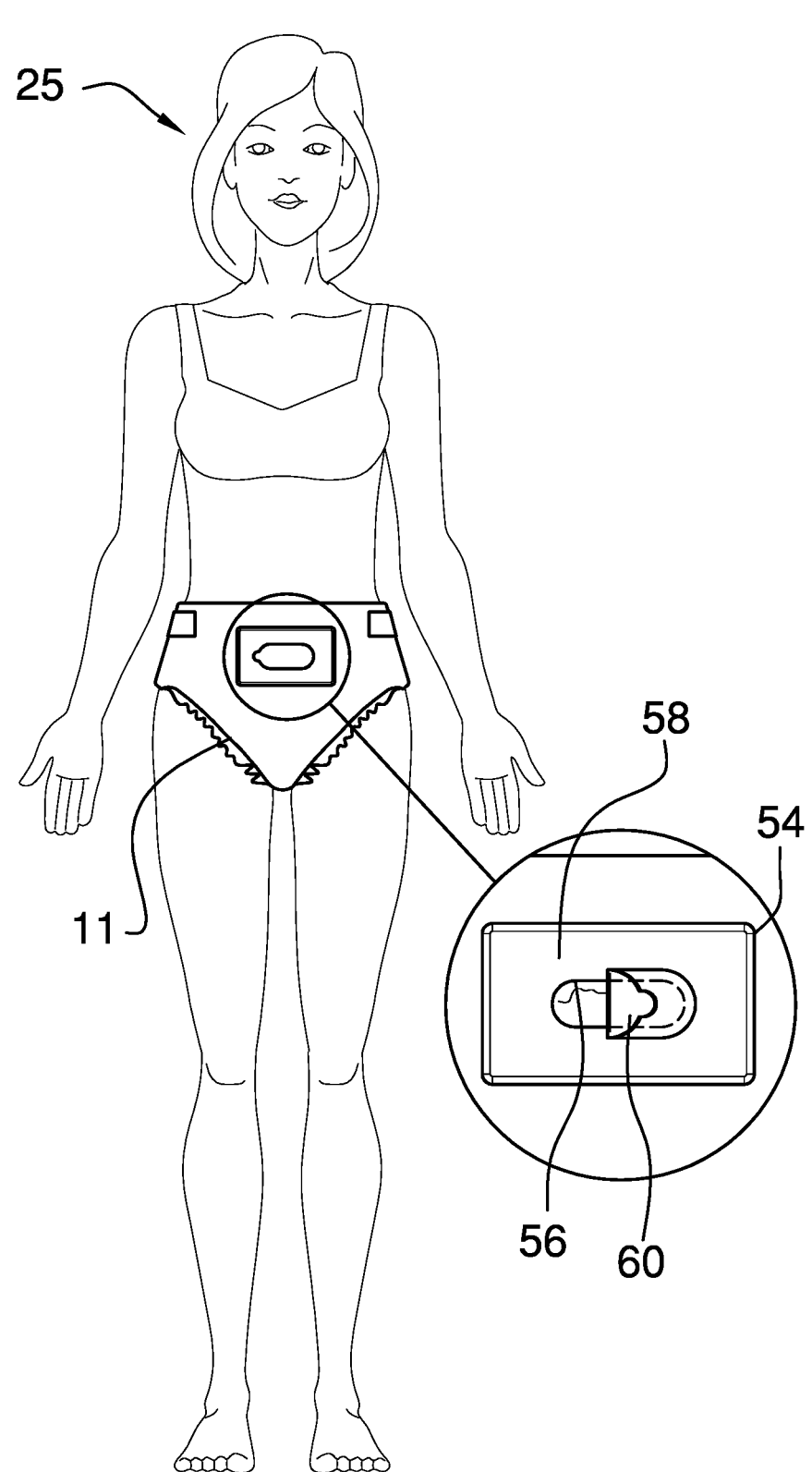
FIG. 7 is a front in-use view of an embodiment of the disclosure showing a first diaper being worn on an adult.

As is most clearly shown in FIG. 7, a container 54 is mounted to the bottom surface 16 of the first diaper 11 in the event that the first diaper 11 is sized for an adult. The container 54 has a dispensing hole 56 in an exposed wall 58 of the container 54 to facilitate the wipes 52, which are contained in the container 54, to be dispensed through the dispensing hole 56. Additionally, a resealable cover 60 is attached to the exposed wall 58 of the container 54 for closing the dispensing hole 56.

A second pouch 62 is attached to the first diaper 11 and the second pouch 62 is applied to the bottom surface 16 of the first diaper 11. The second pouch 62 is spaced from the top side 18 of the perimeter edge 17 of the first diaper 11 and the second pouch 62 has a flap 64 that is foldable over the second pouch 62 for closing the second pouch 62. A storage bag 66 is contained in the second pouch 62 and the second diaper 33 is insertable into the storage bag 66 when the second diaper 33 is removed from the first diaper 11 thereby facilitating the second diaper 33 to be disposed of. Furthermore, the storage bag 66 is comprised of a fluid impermeable material to inhibit the bodily fluids in the second absorbent pad 44 from leaking from the storage bag 66. A pair of second mating members 68 is each attached to a respective one of the second pouch 62 and the flap 64 associated with the second pouch 62. The pair of second mating members are matable to each other for closing the second pouch 62.

In use, the first diaper 11 and the second diaper 33 are placed on the user 25 to facilitate the user 25 to urinate and defecate in the second diaper 33. The first diaper 11 and second diaper 33 are removed from the user 25 when user 25 urinates or defecates in the second diaper 33 and the second diaper 33 is torn away from the first diaper 11. The storage bag 66 is removed from the second pouch 62 and the second diaper 33 is placed in the storage bag 66 for disposal. As many wipes 52 as needed are removed from the first pouch 48 to clean the user 25 and the first diaper 11 is placed back on the user 25. In this way the user 25 can once again have a clean diaper to wear for subsequent urination and defecation thereby eliminating the need for the caregiver 53 to carry a replacement diaper. In this way the caregiver 53 can change a diaper on an infant while the caregiver 53 is in an airport, for example, or other location that the caregiver 53 would not be likely to carry extra diapers.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A multiple use diaper assembly which has a first diaper removably attached to a second diaper thereby facilitating changing of diapers on a user without having to carry additional diapers, said assembly comprising:

a first diaper having a pair of leg scallops wherein said first diaper is configured to be worn on a user's crotch such that each of said leg scallops accommodates a respective one of the user's legs;

a first absorbent pad being attached to said first diaper, said first absorbent pad being comprised of a fluid absorbent material, said first absorbent pad being located on said first diaper wherein said first absorbent pad is configured to absorb bodily fluids from the user;

a pair of tabs, each of said tabs being attached to said first diaper, each of said tabs wrappable onto said first diaper when said first diaper is being worn wherein said pair of tabs is configured to retain said first diaper on the user;

a second diaper being removably attached to said first diaper wherein said second diaper is configured to rest against the user when said first diaper and said second diaper are worn on the user, said second diaper having a pair of leg scallops wherein said pair of legs scallops associated with said second diaper are configured to accommodate the user's legs when said first diaper is worn on the user, a second absorbent pad being attached to said second diaper, said second absorbent pad being comprised of a fluid absorbent material, said second absorbent pad being located on said second diaper wherein said second absorbent pad is configured to absorb bodily fluids from the user;

a first pouch being attached to said first diaper;

a second pouch being attached to said first diaper;

a plurality of wipes, each of said plurality of wipes being stored in said first pouch wherein each of said plurality of wipes is configured to be accessible to a caregiver of the user when the caregiver removes said second diaper from said first diaper when said first absorbent pad has become soiled with bodily fluids, each of said plurality of wipes being pre-moistened wherein each of said plurality of wipes is configured to clean the user of bodily fluids;

a storage bag being contained in said second pouch, said second diaper being insertable into said storage bag when said second diaper is removed from said first diaper thereby facilitating said second diaper to be disposed of, said storage bag being comprised of a fluid impermeable material wherein said storage bag is configured to inhibit the bodily fluids in said second absorbent pad to leak from said storage bag;

wherein said first diaper has a top surface and a bottom surface and a perimeter edge extending between said top surface and said bottom surface, said perimeter edge having a top side, a bottom side, a first lateral side and a second lateral side, each of said first lateral side and said second lateral side having a curved portion which curves toward each other such that curved portion of each of said first lateral side and said second lateral side defines a respective one of said leg scallops, said curved portion of each of said first lateral side and said second lateral side being centrally positioned between said top side and said bottom side; and wherein said assembly includes a pair of adhesive strips, each of said adhesive strips being applied to said top surface of said first diaper, each of said pair of adhesive strips being aligned with said perimeter edge of said first diaper.

2. The assembly according to claim 1, wherein:

said assembly includes a pair of elastomeric bands, each of said elastomeric bands being attached to said top surface of said first diaper, each of said pair of elastomeric bands being aligned with said curved portion of a respective one of said first lateral side and said second lateral side wherein each of said pair of elastomeric bands is configured to enclose each of said leg scallops around the respective user's leg;

a first one of said pair of adhesive strips extends along said bottom side of said perimeter edge and along each of said first lateral side and said second lateral side of said perimeter edge and terminating at said pair of elastomeric bands; and a second one of said pair of adhesive strips extends along said top side of said perimeter edge and along each of said first lateral side and said second lateral side of said perimeter edge and terminating at said pair of elastomeric bands.

3. The assembly according to claim 1, wherein:

said first diaper has a perimeter edge which has a first lateral side and a second lateral side and a top side and a bottom side, each of said first lateral side and said second lateral side having a curved portion;

each of said tabs is positioned on a respective one of said first lateral side and said second lateral side of said perimeter edge of said first diaper;

each of said tabs is positioned between said curved portion of said respective first lateral side and second lateral side and said top side of said perimeter edge; and each of said tabs has a first surface, each of said pair of tabs having an adhesive pad being applied to said first surface, said adhesive pad on each of said pair of tabs adhesively engaging said bottom surface of said first diaper when said pair of tabs are wrapped onto said first diaper.

4. The assembly according to claim 1, wherein:

said second diaper has an upper surface and a lower surface and an outside edge extending between said upper surface and said lower surface, said outside edge having an upper side, a lower side, a first sidelong side and a second sidelong side;

each of said first sidelong side and said second sidelong side has a curved portion which curves toward each other such that curved portion of each of said first sidelong side and said second sidelong side defines a respective one of said leg scallops associated with said second diaper;

said curved portion of each of said first sidelong side and said second sidelong side is centrally positioned between said upper side and said lower side; and said lower surface is adhered to each of said pair of adhesive strips on said first diaper thereby removably retaining said second diaper on said first diaper having said outside edge of said second diaper being aligned with said perimeter edge of said first diaper.

5. The assembly according to claim 1, wherein:

said first diaper has a bottom surface and a perimeter edge; and said first pouch is applied to said bottom surface of said first diaper, said first pouch being spaced from a bottom side of said perimeter edge of said first diaper, said first pouch having a flap being foldable over said first pouch for closing said first pouch.

6. The assembly according to claim 1, wherein:

said first diaper has a bottom surface and a perimeter edge; and said second pouch being applied to said bottom surface of said first diaper, said second pouch being spaced from a top side of said perimeter edge of said first diaper, said second pouch having a flap being foldable over said second pouch for closing said second pouch.

7. A multiple use diaper assembly which has a first diaper removably attached to a second diaper thereby facilitating changing of diapers on a user without having to carry additional diapers, said assembly comprising:

a first diaper having a pair of leg scallops wherein said first diaper is configured to be worn on a user's crotch such that each of said leg scallops accommodates a respective one of the user's legs, said first diaper having a top surface and a bottom surface and a perimeter edge extending between said top surface and said bottom surface, said perimeter edge having a top side, a bottom side, a first lateral side and a second lateral side, each of said first lateral side and said second lateral side having a curved portion which curves toward each other such that curved portion of each of said first lateral side and said second lateral side defines a respective one of said leg scallops, said curved portion of each of said first lateral side and said second lateral side being centrally positioned between said top side and said bottom side;

a pair of elastomeric bands, each of said elastomeric bands being attached to said top surface of said first diaper, each of said pair of elastomeric bands being aligned with said curved portion of a respective one of said first lateral side and said second lateral side wherein each of said pair of elastomeric bands is configured to enclose each of said leg scallops around the respective user's leg;

a first absorbent pad being attached to said first diaper, said first absorbent pad being comprised of a fluid absorbent material, said first absorbent pad being located on said first diaper wherein said first absorbent pad is configured to absorb bodily fluids from the user, said first absorbent pad having a bonded surface being bonded to said top surface of said first diaper, said first absorbent pad being elongated to extend substantially between said top side and said bottom side of said perimeter edge of said first diaper, said first absorbent pad being centrally positioned between said first lateral side and said second lateral side of said perimeter edge;

a pair of tabs, each of said tabs being attached to said first diaper, each of said tabs wrappable onto said first diaper when said first diaper is being worn wherein said pair of tabs is configured to retain said first diaper on the user, each of said tabs being positioned on a respective one of said first lateral side and said second lateral side of said perimeter edge of said first diaper, each of said tabs being positioned between said curved portion of said respective first lateral side and second lateral side and said top side of said perimeter edge, each of said tabs having a first surface, each of said pair of tabs having an adhesive pad being applied to said first surface, said adhesive pad on each of said pair of tabs adhesively engaging said bottom surface of said first diaper when said pair of tabs are wrapped onto said first diaper;

a pair of adhesive strips, each of said adhesive strips being applied to said top surface of said first diaper, each of said pair of adhesive strips being aligned with said perimeter edge of said first diaper, a first one of said pair of adhesive strips extending along said bottom side of said perimeter edge and along each of said first lateral side and said second lateral side of said perimeter edge and terminating at said pair of elastomeric bands, a second one of said pair of adhesive strips extending along said top side of said perimeter edge and along each of said first lateral side and said second lateral side of said perimeter edge and terminating at said pair of elastomeric bands;

a second diaper being removably attached to said first diaper wherein said second diaper is configured to rest against the user when said first diaper and said second diaper are worn on the user, said second diaper having a pair of leg scallops wherein said pair of legs scallops associated with said second diaper are configured to accommodate the user's legs when said first diaper is worn on the user, said second diaper having a upper surface and a lower surface and an outside edge extending between said upper surface and said lower surface, said outside edge having a upper side, a lower side, a first sidelong side and a second sidelong side, each of said first sidelong side and said second sidelong side having a curved portion which curves toward each other such that curved portion of each of said first sidelong side and said second sidelong side defines a respective one of said leg scallops associated with said second diaper, said curved portion of each of said first sidelong side and said second sidelong side being centrally positioned between said upper side and said lower side, said lower surface being adhered to each of said pair of adhesive strips on said first diaper thereby removably retaining said second diaper on said first diaper having said outside edge of said second diaper being aligned with said perimeter edge of said first diaper;

a second absorbent pad being attached to said second diaper, said second absorbent pad being comprised of a fluid absorbent material, said second absorbent pad being located on said second diaper wherein said second absorbent pad is configured to absorb bodily fluids from the user, said second absorbent pad having a bonded surface being bonded to said upper surface of said second diaper, said second absorbent pad being elongated to extend substantially between said upper side and said lower side of said outside edge of said second diaper, said second absorbent pad being centrally positioned between said first sidelong side and said second sidelong side of said outside edge;

a first pouch being attached to said first diaper, said first pouch being applied to said bottom surface of said first diaper, said first pouch being spaced from said bottom side of said perimeter edge of said first diaper, said first pouch having a flap being foldable over said first pouch for closing said first pouch;

a second pouch being attached to said first diaper, said second pouch being applied to said bottom surface of said first diaper, said second pouch being spaced from said top side of said perimeter edge of said first diaper, said second pouch having a flap being foldable over said second pouch for closing said second pouch;

a plurality of wipes, each of said plurality of wipes being stored in said first pouch wherein each of said plurality of wipes is configured to be accessible to a caregiver of the user when the caregiver removes said second diaper from said first diaper when said first absorbent pad has become soiled with bodily fluids, each of said plurality of wipes being pre-moistened wherein each of said plurality of wipes is configured to clean the user of bodily fluids; and a storage bag being contained in said second pouch, said second diaper being insertable into said storage bag when said second diaper is removed from said first diaper thereby facilitating said second diaper to be disposed of, said storage bag being comprised of a fluid impermeable material wherein said storage bag is configured to inhibit the bodily fluids in said second absorbent pad to leak from said storage bag.

* * * * *